(12) United States Patent
Pike et al.

(10) Patent No.: US 9,211,203 B2
(45) Date of Patent: Dec. 15, 2015

(54) HINGE FOR MEDICAL DEVICE

(71) Applicants: Kelly A. Pike, Half Moon Bay, CA (US); Boris Anukhin, San Jose, CA (US)

(72) Inventors: Kelly A. Pike, Half Moon Bay, CA (US); Boris Anukhin, San Jose, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 121 days.

(21) Appl. No.: 13/722,722

(22) Filed: Dec. 20, 2012

(65) Prior Publication Data
US 2014/0180396 A1 Jun. 26, 2014

(51) Int. Cl.
- *A61F 2/82* (2013.01)
- *A61F 2/01* (2006.01)
- *A61B 17/12* (2006.01)
- *A61B 17/00* (2006.01)

(52) U.S. Cl.
CPC .............. *A61F 2/82* (2013.01); *A61B 17/12145* (2013.01); *A61B 2017/00588* (2013.01); *A61F 2/01* (2013.01)

(58) Field of Classification Search
CPC .................. A61F 2230/0086; A61F 220/0008; A61F 2220/0091; A61F 2/82
USPC ............ 606/157, 158, 200; 623/1.15–1.2, 1.3
See application file for complete search history.

(56) References Cited

U.S. PATENT DOCUMENTS

| | | | |
|---|---|---|---|
| 6,312,460 B2 | 11/2001 | Drasler et al. | |
| 7,241,304 B2 | 7/2007 | Boyle et al. | |
| 7,842,064 B2 | 11/2010 | Huter et al. | |
| 2007/0168010 A1 | 7/2007 | Goshgarian | |
| 2007/0233183 A1* | 10/2007 | Brady et al. | 606/200 |
| 2007/0299505 A1* | 12/2007 | Gregorich et al. | 623/1.15 |
| 2008/0097583 A1 | 4/2008 | Shanley et al. | |
| 2008/0221664 A1* | 9/2008 | Bales et al. | 623/1.22 |
| 2010/0217380 A1 | 8/2010 | Donovan et al. | |

* cited by examiner

*Primary Examiner* — Thomas McEvoy
(74) *Attorney, Agent, or Firm* — Workman Nydegger; Randy Shen (57) ABSTRACT

A device is provided that provides flexibility to an assembly. The device includes a loop hinge that hinges by twisting a body of the loop hinge.

29 Claims, 5 Drawing Sheets

HINGE FOR MEDICAL DEVICE

BACKGROUND OF THE INVENTION

In many medical procedures, there is a need to use devices in relatively small spaces or in constrained environments. Through an arteriotomy in a vessel, procedures such as angioplasties are performed. Medical devices are deployed and secured through a relatively small opening in the vessel.

In order to introduce medical devices through a small opening, it is often necessary to change the shape or configuration of the medical device prior to using or deploying the medical device. Some medical devices are formed of memory material that enables a device to return to an original state or configuration after being deployed.

During some of the procedures, the devices being deployed are often arranged in a pre-deployment position. Stents, for example, are often compressed in order facilitate the placement and deployment of the stent. Compressing the stent can change the shape of the stent such that the stent can be more easily introduced into the patient's vasculature and maneuvered to the appropriate location.

When the stent is actually deployed, the stent expands from its compressed state to a deployed state. The expansion is achieved by removing the compressing force. For instance, a stent held in a distal end of a deployment device is expelled from the distal end. As the stent exits the deployment device, the compressing or deforming force is removed and the stent returns to an original shape. The ability to deploy a device that can change from a pre-deployed or compressed state to a deployed state can make the procedure easier and less burdensome on the patient.

One of the problems facing devices that can transition from one state to another state relates to the ability of the device to bend or compress. Stents and other devices are often configured with portions that are positioned and configured to bend. A strut of a stent, for example, may be bent along its length and is similar to a leaf spring. A leaf spring, however, has a somewhat limited range of motion and bending a strut in this manner can place excessive strain on the strut or on the device itself. Other devices, such as locators, embolic filter cages, and mitral clips include potions or components that bend, for example during deployment or use of the device.

BRIEF SUMMARY OF THE INVENTION

Embodiments relate to medical devices including hinges and to systems, methods, and devices that incorporate hinges. In one example, an integrated hinge that hinges using a twisting or torsional motion that can provide a greater range of motion at a lower strain, compared to simply bending a flat strip.

In one example, the device includes an integrated loop hinge whose body includes a first arm, a second arm and a body. The loop connects the first arm with the second arm and hinge points are formed where the arms join the loop. The device hinges by twisting at the hinge points. The hinge points can be torsional hinge points.

In another example, the body of the device includes a first arm having a first outer end and a first inner end and a second arm having a second outer end and a second inner end. A loop connects the inner ends of the first arm with the second arm. The first arm and the second arm are configured to rotate relative to the loop. Rotation of the first arm and the second arm twists the body to perform a hinge action that changes an orientation of the first arm relative to the second arm.

In another example, the device or loop hinge may be incorporated into a larger device that includes a distal end and a proximal end. The loop hinge may be disposed between the distal and proximal ends of the larger device. Movement of the distal end towards the proximal end twists the body effective to hinge the loop hinge. The loop hinge can be oriented in any direction relative to the distal and proximal ends of the device. In one example, the loop hinge may be disposed between other components of the larger device.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

The invention will be described and explained with additional specificity and detail through the use of the accompanying drawings in which.

DETAILED DESCRIPTION OF THE PREFERRED EMBODIMENTS

Embodiments of the invention relate to devices that include portions or components that move relative to other portions or components. More particularly, embodiments of the invention relate to hinges and to medical devices that include hinges. Stents, locator feet, embolic filter cages, mitral clips, and the like are examples of medical devices that may include a hinge or component that provides hinge-like motion. Embodiments of devices capable of hinge or hinge-like motion disclosed herein can be implemented in devices that can move from a first (e.g., contracted or compressed) position to a second (e.g., expanded or unbiased) position or vice versa. Embodiments achieve the transition from a first position to a second position by configuring the body of the device such that twisting the body or portions thereof results in a change in position via a hinging motion.

Embodiments relate, by way of example, to a single piece, elastic hinge device or hinge. The hinge may be configured to move from an unbiased position to a biased position under the influence of a force. When the force is removed, the hinge returns to the unbiased position. The force can change the position and cause the hinging motion by effectively twisting the body of the device. In one example, torsional motion of the body of the device or a portion thereof results in a hinging motion of the device.

More specifically, embodiments disclosed herein hinge (or bend, flex, rotate) using a twisting or torsional motion. The body of the hinge achieves a hinging action when the body is twisted or when a portion of the body is twisted relative to another portion of the hinge body. Hinging a device with a twisting or torsional motion can produce a higher angle of deflection and a greater range of hinge motion. In addition, the hinging motion can be achieved at a lower strain compared to bending a flat strip or compared to a leaf spring type hinge.

Embodiments relate to a hinge device that provides a greater range of motion than conventional hinges such as leaf spring hinges. The ability to flex or bend with an improved range of motion can improve the functionality of medical devices, for example when the devices are used within a limited or constrained space. Embodiments can make procedures easier to perform, and may reduce the trauma experienced by the patient during a procedure.

FIG. 1 illustrates a perspective view of a loop hinge 100 in accordance with embodiments of the invention. The loop hinge 100 is an example of a hinge device. The loop hinge 100 has a body that includes an arm 102, an arm 104 and a loop 106. The arm 102 and the arm 104 are connected by the loop 106. The arm 102 includes an outer end 122 and an inner end 120. The arm 104 similarly includes an outer end 126 and an inner end 124. The inner ends 122 and 124 are nearest the loop 106 and are separated by a gap 110.

Figure 1A:
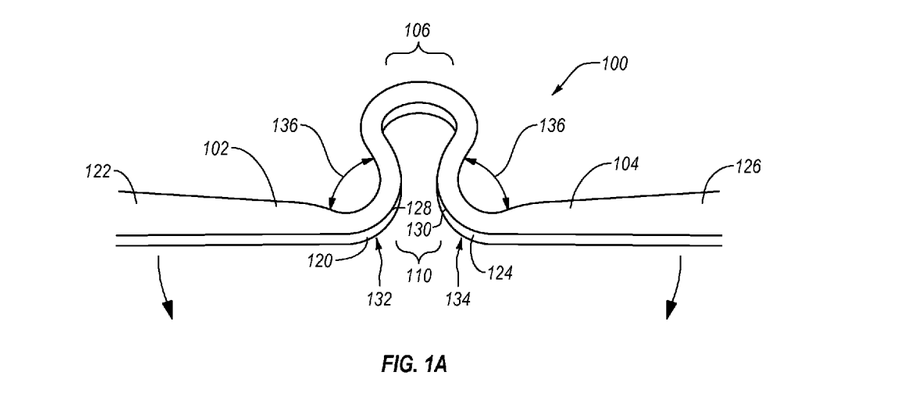
FIG. 1A schematically illustrates a perspective view of a hinge device.

The arm 102 can be configured to be identical or substantially similar to the arm 104. Alternatively, the arm 102 can be differently configured from the arm 104. For instance, a length of the arm 102 can be the same or different than a length of the arm 104. A shape of the arm 102 (e.g., cross-sectional shape, cross sectional area, length) can be the same or different than a shape of the arm 104. In addition, the shapes or dimensions of the arms 102, 104, and of the loop 106, can vary along their length.

When the loop hinge 100 is integrated as a component of a larger device, the shape of the body of the loop hinge 100 or any portion thereof may be influenced by the shape of the larger device. The outer ends 122 and 126 may differ in size, shape and/or configuration from the size, shape, and or configuration of the inner ends 120 and 124.

The loop hinge 100 is may be formed of an elastic or memory material. The material may be a memory material (e.g., Nitinol or other alloy or plastic) such that the hinge 100, after being biased or deformed by a force, returns to an original position or shape when the force is removed. The loop hinge 100 may be formed of many different materials including, but not limited to, elastic or memory materials, spring materials L605, elgiloy, 17-7 PH, or the like or any combination thereof.

During manufacture of the hinge 100, any portion of the loop hinge 100 can be set in any position relative to any other portion of the loop hinge. In one example of a first or unbiased position, the loop hinge 100 may be substantially planar such that the arm 102, the arm 104 and the loop 106 lie in substantially the same plane. In addition, the arm 102 and the arm 104 can be arranged in substantially the same line, with the loop 106 extending to the side of that line.

Any of the arm 102, the arm 104, and/or the loop 106 may also be in a different plane in the unbiased position. The arm 102 can be angled with respect to the arm 104. Also, the loop 106 could be angled and non-planar with respect to the arm 102 and/or the arm 104.

FIG. 1 further illustrates that the arm 102 and the arm 104 are substantially straight in this example. However, the arm 102 and/or the arm 104 may include one or more bends or curves. The loop 106 may in addition be configured to have different shapes and configurations.

The loop hinge 100 can be incorporated into a larger medical device. The outer ends 122 and 126 may be integrated with other aspects of the larger medical device. The loop hinge 100, for example, may be incorporated in a locator foot, a filter cage, a mitral clip, a stent, or the like or other device whose shape or orientation is changed from one position to another position. For example, the loop hinge 100 enables a larger medical device to flex, hinge, or deform from one position to another position.

The inner end 120 and the inner end 124 of the loop hinge 100 are separated by a gap 110. The configuration of gap 110 is partially determined by the configuration of the loop 106. A length of the gap 110, for example, is determined by the configuration of the loop 106. As a result, the length or dimensions of the gap 110 can be set during manufacture of the loop hinge 100. In addition, the shape of the loop 106 can also be determined during manufacture. The loop 106 may be circular, elliptical, square, or the like. The sides of the loop 106 can be symmetrical or asymmetrical.

The loop hinge 100 further includes a hinge point 132 and a hinge point 134, which are examples of torsional hinge points. The hinge points 132 and 134 are formed by a bend or turn in the body of the loop hinge 100. By forming a bend at the hinge points 132 and 134, rotation of the arms 102 and 104 cause the body to twist substantially at the hinge points 132 and 134. As a result, the loop hinge 100 can bend or hinge when the body is twisted. The rotation of the arms 102 and 104 creates torsional movement in the body of the loop hinge 100 at the hinge points 132 and 134.

The angle 136 between the arm 102 and the loop 106 can be acute or obtuse and may depend on the desired configuration of the loop hinge 100 and/or a device in which the loop hinge 100 is integrated. A similar angle may be present between the arm 104 and the loop 106.

The hinge points 132 and 134 are located at ends of the gap 110. Alternatively stated, the hinge points 132 and 134 are located at the inner ends 120 and 124 of, respectively, the arms 102 and 104. The gap 110 separates the hinge point 132 from the hinge point 134. When the loop hinge 100 hinges, the loop hinge 100 enables the arm 102 and/or the arm 104 to move relative to the loop 106 at, respectively, the hinge point 132 and/or the hinge point 134. Hinging can be achieved by rotating only one of the arms 102 or 104. By forming bends at the hinge points 132, 134, the loop hinge 100 can achieve a hinge action or a bending action by torsional twisting at least at the hinge points 132 and 134.

Figure 1B:
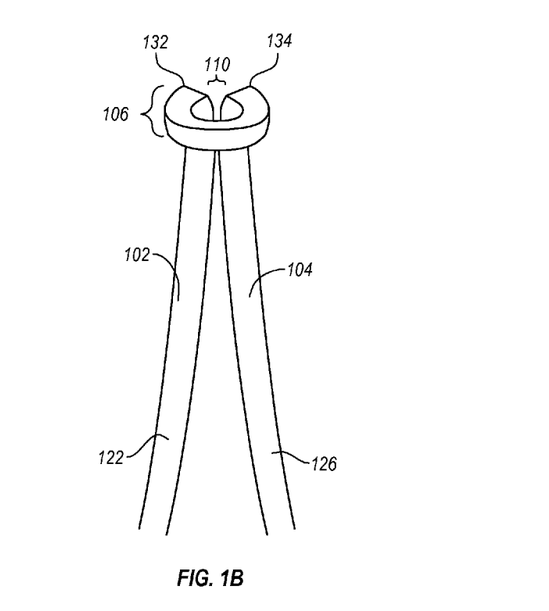
FIG. 1B schematically illustrates a perspective view of the hinge device in a hinged position.

FIG. 1B illustrates an example of the loop hinge 100 in a hinged, bent, or biased position. The loop hinge 100 is biased, in one example, by bringing the outer end 122 of the arm 102 and/or the outer end 126 of the arm 104 towards the other. In one example, the arm 102 and the arm 104 are rotating about, respectively, the hinge points 132 and 134. However, rotation actually twists the body of the loop hinge at the hinge points 132 and 134 in part because the hinge points 132 and 134 correspond to bends or turns in the body of the loop hinge 100. The arms 102 and 104 can rotate in the same direction or different directions when moving to the biased position and the loop hinge 100 can accommodate multiple configurations.

As the loop hinge 100 is moved from the unbiased position shown in FIG. 1A to the biased position shown in FIG. 1B, the relative positions of the arm 102, the arm 104, and the loop 106 change such that the arm 102, the arm 104, and the loop 106 may no longer in the same plane. If the arm 102, the arm 104, and the loop 106 were not in the same plane in the unbiased position, the relative positions still change when transitioning the loop hinge from one position to another position.

Figure 1C:
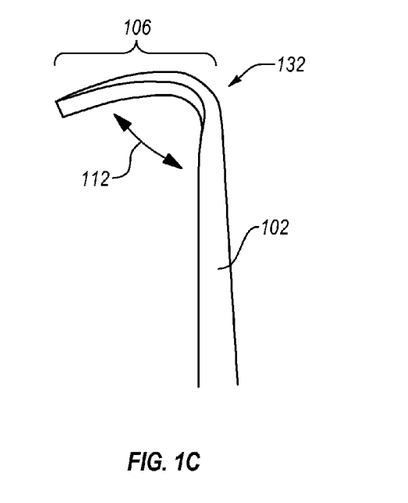
FIG. 1C schematically illustrates a side view of the hinge device in a hinged position.

FIGS. 1B and 1C schematically illustrate examples of the loop hinge 100 in a hinged or biased position from different perspectives. FIG. 1C schematically illustrates that the loop 106 is angled at an angle 112 relative to the arm 102 and/or the arm 104 when in the biased position. This is caused by the twisting the body at the hinge points 132 and 134 to change the orientation of the loop hinge 100, which can be achieved by rotating the arms about the hinge points 132 and 134. Rotation of the arm 102 and/or the arm 104 causes the body of the loop hinge 100 to twist as previously discussed.

Thus, forming the loop 106 between the arm 102 and the arm 104 allows the hinge action to be achieved by twisting or torsional movement, at hinge points 132 and 134, rather than simply bending, for example, arms 102 and/or 104, like a conventional leaf spring. More specifically, forming the loop 106 such that a bend in the body of the loop hinge is present at the hinge points 132 and 134 enables the hinge action to be achieved by twisting the body. Thus, rotation of the arm 102 and/or 104 twists the body of the loop hinge 100. In this example, movement of the arm 102 causes the loop hinge 100 to twist substantially at the hinge point 132. Similarly, twisting occurs at the hinge point 134 as the arm 104 of the loop hinge 100 moves from an initial unbiased position to a hinged or biased position.

Figure 1D:
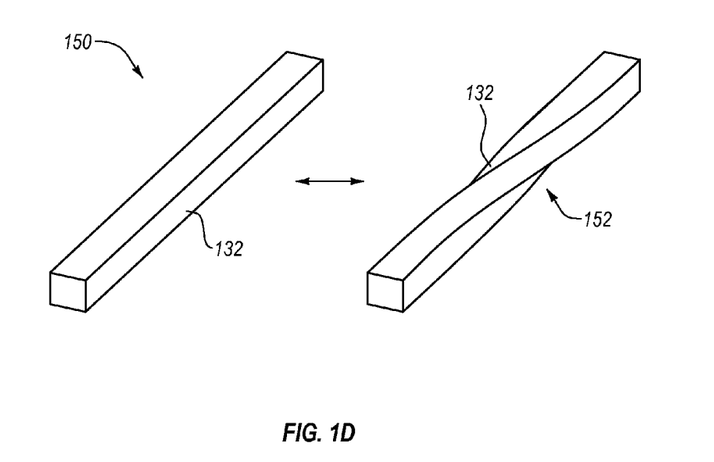
FIG. 1D schematically illustrates schematically a body of the hinge device twisting to accomplish a hinging motion.

FIG. 1D schematically illustrates an example of how the hinging is achieved in the loop hinge by twisting the body and illustrates the transition from one position to another position. FIG. 1D schematically illustrates the hinge point 132 in an unbiased position 150 and a biased position 152 and illustrates the torsional movement of the body as the arms 102 and 104 rotate to achieve a hinging effect.

FIG. 1D schematically illustrates that rotation of the arm 102 causes the body of the loop hinge 100 to twist as illustrated by the biased position 152. In this way, a hinge action is achieved by twisting the body of the loop hinge 100. More specifically, the body twists at least at the hinge points 132 and 134. The twisting of the body of the loop hinge 100 may not occur solely at the hinge points 132 and 134, but may extend at least partially into the loop 106 and or the connected arm 102 and/or 104.

The loop hinge 100 may be formed of a memory material (e.g., Nitinol).

The memory of the material enables the loop hinge 100 to return to the unbiased position whenever a deforming force applied to the loop hinge 100 is removed. In one example, a force may be required to cause the loop hinge 100 to hinge to the position shown, for example, in FIG. 1B. When the force is removed, the loop hinge 100 returns to the resting or unbiased position shown in FIG. 1A.

Because the hinge movement is achieved by twisting the arm 102 and/or the arm 104 at, respectively, the hinge points 132 and 134, a greater range of movement can be achieved compared, for example to a leaf hinge. Advantageously, the loop hinge 100 can achieve a higher angle of deflection and a greater range of hinge motion at a lower strain compared to bending a flat strip (e.g., a leaf hinge).

In one example, the bending of the arm 102, 104 and twisting of the hinge point 132, 134 occur simultaneously. As the arm 102 is moved, the body of the hinge 100 begins to twist at the hinge point 132 at the same time. In one example, a height and width of a cross section of the loop hinge 100 can result in efficient translation of the hinging action.

In one example, the cross-sectional height and width may be equal or nearly equal in a vicinity of or at the hinge points 132 and 134 because this is the location where the twisting substantially occurs. As a result, the cross-sectional height and width of other locations of the loop hinge 100 (e.g., of the outer ends 122 and 126) may be different. This enables the shape of the arms 102 and 104 and of portions of the loop 106 to vary while still achieving an efficient hinging action at the hinge points of the loop hinge 100.

A length of the loop 106 can impact a force that is required to bend the loop hinge 100. As the length of the loop 106 increases, the force required to hinge is reduced. In one example, the configurations (e.g., materials, dimensions) of the arms 102, 104, loop 106, and/or hinge points 132, 134 can be selected according to the device into which the loop hinge is incorporated, the location at which the loop hinge 106 is deployed, the type of material used in forming the loop hinge 106, or the like or any combination thereof.

In one example, the loop hinge 106 can achieve a greater range of motion (e.g., compared to a leaf spring) with less strain. The greater range of motion can be attributed to multimode distortion. As discussed herein, the loop hinge 100 both bends and twists. This relieves the need for the hinge distortion to be accomplished entirely be bending as is the case in a leaf spring. Further, more bending concentrates strain on the edge layer of the member (the leaf spring) thereby limiting the maximum amount of strain which can be endured by the device. Bending a leaf spring can result in excessive strain on the outer layer, which may result in failure. In contrast, twisting the body of the loop hinge 100 is carried by the entire volume of the loop hinge (e.g., the arm 102 and the loop 106 and not just an outer layer of the hinge 100. As a result, a greater range of motion with less strain can be achieved.

The loop hinge 100 may be formed from a single body that is shaped in an appropriate manner. The loop hinge 100 can be configured in a variety of different positions and orientations. In one example, by forming the loop 106 between the arms 102 and 104 such that all are in the same plane, rotation of the arms 102 and 104 twists the body at least at the hinge points 132 and 134 and causes the relative orientations of the arms 102, 104 and the loop 106 to change. When in a biased position, an angle 112, as illustrated in FIG. 1C, is formed between the loop 106 and the arm 102 and/or 104. The angle 112 may be different from an angle 136 between the arm 102 and the end of the loop 106 shown in FIG. 1A in an unbiased position.

Figure 1E:
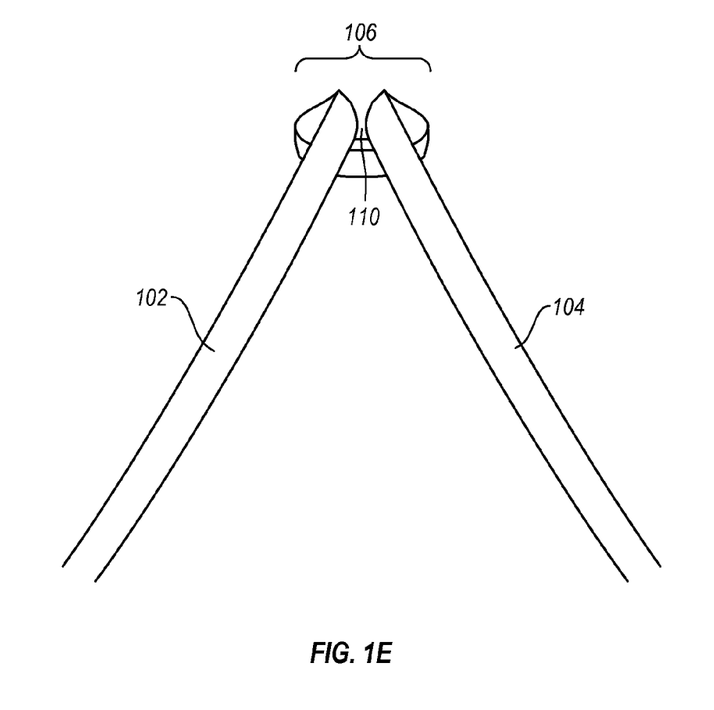
FIG. 1E schematically illustrates the hinge device as the hinge device moves from one position to another position.

FIG. 1E schematically illustrates the loop hinge 100 in the process of being moved from an unbiased position to a biased position or vice versa. When the loop hinge 100 transitions from one position to another position as shown in FIG. 1E, dimensions of the gap 110 may change during actuation of the loop hinge 100. When the loop hinge 100 moves from the unbiased position (e.g., shown in FIG. 1A) to the biased position (e.g., shown in FIG. 1B), the gap 110 may shorten during the transition. The inner end 120 of the arm 102 may move towards and/or contact the inner end 124 of the arm 104 during operation or actuation of the loop hinge 100.

Thus, the gap 110 may expand and/or contract during transition of the loop hinge 100 from one position to another position. The body 100, which may be formed of a memory material, may cause the gap 110 to lengthen/shorten once the biased position is reached (or before or during transition). In other words, the dimensions of the gap 110 may change (e.g., lengthen and/or shorten) when the loop hinge 100 is moving from one position to another position.

More generally, the dimensions of the gap 110 may change during operation of the loop hinge 100. As the loop hinge 100 reaches its final biased position, the dimensions of the gap 110 may have changed to be different from the dimensions of the gap 110 when the loop hinge 100 is unbiased Alternatively, the memory of the loop 106 may cause the gap 110 to return to its original dimension in the biased position.

When the loop hinge 100 begins to transition from the unbiased position to the biased position, a force may be applied at the outer ends 122 and 126 of the arms 102 and 104. Because the loop hinge 100 is initially planar, this force may cause the gap 110 to shorten as discussed herein. Once the loop hinge 100 reaches the biased position, the force may no longer be directed directly at the loop 106. As a result, any change in the dimensions of the gap 110 may be reversed by the memory of the loop 106 when the loop hinge 100 is in the biased position.

When the loop hinge 100 begins to transition from the unbiased position to the biased position, a force may be applied at the outer ends 122 and 126 of the arms 102 and 104. This may cause the arms 102 and 104 to bend before or at the same time that the body twists at the hinge points 132 and 134. In this case, the arms 102 and 104 may be more stiff if desired to help prevent the arms 102 and 104 from bending during the transition of the loop hinge 100 from one position to another position. Thus, the material composition of the arms 102 and 104 may be the same as or different from the material composition of the loop 106 and/or the hinge points 132 and 134.

Figure 2A:
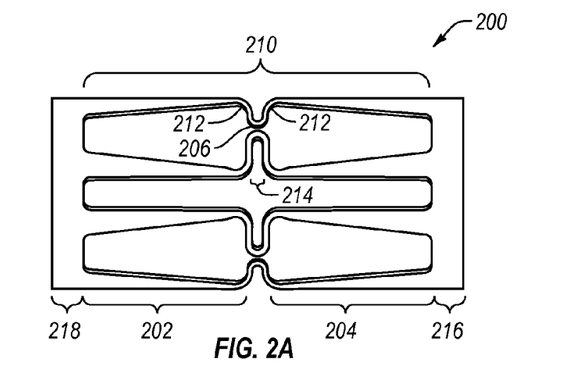
FIG. 2A schematically illustrates a locator foot that includes multiple hinge devices in unbiased positions.
Figure 2B:
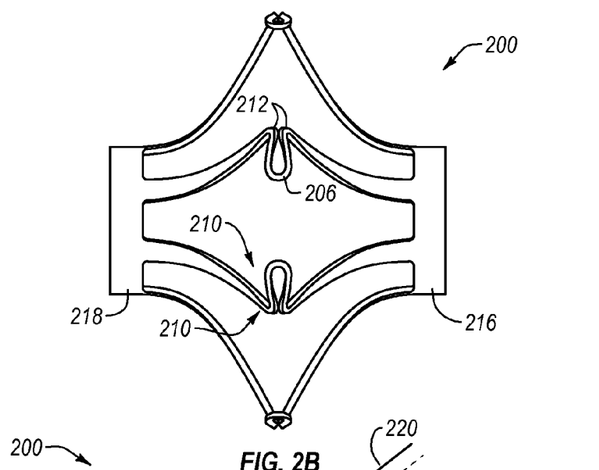
FIG. 2B schematically illustrates the locator foot when the hinge devices are in biased positions.
Figure 2C:
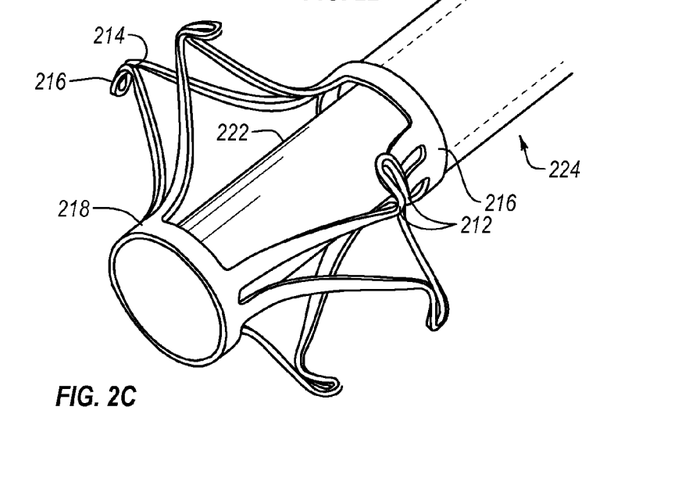
FIG. 2C schematically illustrates the locator foot integrated in a distal end of a medical device.

FIG. 2A illustrates an example of loop hinges integrated in a medical device such as a locator foot. FIG. 2B illustrates the medical device with the loop hinges in biased positions. FIG. 2C illustrates a perspective view of the distal end of a medical device that includes a locator foot.

FIG. 2A illustrates one or more loop hinges 210, which are examples of the loop hinge 100, integrated into a locator 200 (also referred to as a locator foot). The locator 200 is an example of a device that is used to locate, by way of example, a wall of a vessel. For instance, when performing a procedure such as an angioplasty, an arteriotomy is formed in a vessel. After the procedure is completed, it is necessary to close the arteriotomy. The locator 200 can be used with a closure device to close the arteriotomy.

To close the arteriotomy, the locator device is inserted through the arteriotomy and the locator 200 is expanded. When the locator 200 is expanded, the loop hinges 210 extend radially such that the locator 200 becomes larger than the arteriotomy. By retracting the locator 200 with the loop hinges 210 radially extended, the location of the vessel wall can be effectively identified when the biased loop hinges 210 (which are in their biased positions and radially extended) encounter the vessel wall. The closure device can then be deployed once the vessel wall is located. The locator 200 is then released such that the loop hinges 210 open or return to their unbiased positions and the locator 200 can be withdrawn.

The locator 200 includes a distal end 218 and a proximal end 216. The loop hinges 210 extend between the distal end 218 and the proximal end 216. The outer ends of the arms 202 and 204 are integrated with, respectively, the distal end 218 and the proximal end 216 of the locator 200.

The locator 200 can selectably engage an inner surface of the blood vessel wall adjacent to the arteriotomy. The locator 200 is configured to draw the blood vessel wall taut and can maintain the proper position of an apparatus used in the procedure. The locator 200 can be used, for example, during intromission of a device, during closure of the arteriotomy, or the like.

The locator 200 includes one or more loop hinges 210. As illustrated in FIG. 2A, the loop hinges 210 are disposed along the length of the locator 200 and are arranged with a longitudinal axis of the locator 200. The loop hinges 210 are arranged to be disposed on the perimeter of the locator 200 and are substantially planar with the outer surface of the locator 200. In this example, the arms and loops of each loop hinge are substantially planar in the unbiased position. The distal end 218 of the locator 200 may be configured, for example, with a pigtail to facilitate atraumatic advancement of the distal end 218.

The locator 200 is selectably controllable between an unexpanded or unbiased position and an expanded or biased position. In the unexpanded position, the locator 200 has an unexpanded size and the loop hinges 210 are unbiased such that the locator 200 is substantially tubular. In an expanded or biased position, the loop hinges 210 hinge to expand outwardly as illustrated in FIG. 2B. To hinge the loop hinges 210, the distal end 218 is brought closer to the proximal end 216. This force pushes the arms 202 and 204 of the loop hinges 210 towards each other, which causes, in the context of the locator 200, the loop hinges 210 to extend out radially from the locator 200.

Pushing the distal end 218 towards the proximal end 216 effectively causes the loop hinges 210 to hinge by pushing on the outer ends of the arms 202 and 204. Pushing on the outer ends of the arms 202 and 204 can shorten the gap 214 as previously discussed. The loop hinges 210 hinge or bend, which causes the middle portion or the loop 206 of each loop hinge 210 to move outwardly or radially, thereby expanding the size of the locator 200. By retracting the locator 200 while the loop hinges 210 are biased and the locator 200 has an expanded size, the locator 200 can engage or locate the vessel wall.

In one example, the loop hinges 210 are equally distributed about an outer periphery of the locator 200. In addition, the loop hinges 210 may include radiopaque markers or may be wholly or partially formed from a radiopaque material to facilitate observation of the loop hinges and/or the locator 200 using fluoroscopy or other imaging systems.

Each loop hinge 210 includes an arm 202, an arm 204, and a loop 206 as previously described. Each loop hinge 210 also includes hinge points 212. When the locator 200 is moved to the biased or expanded position, the arms 202 and 204 are effectively rotated about the hinge points 212. As previously stated, the inclusion of the loop 216 and orientation of the loop 216 relative to the arms 202 and 204 causes rotation of the arms 202 and 204 to twist the body of each loop hinge 210 at the hinge points 212. More specifically, pushing the distal end 218 of the locator 200 towards the proximal end 216 causes the loop hinges 210 to twist at the hinge points 212. Twisting the body of the loop hinges 210 in this manner causes the loop hinges 210 to hinge or bend.

More specifically, axial movement of the distal end 218 relative to the proximal end 216 can actuate the loop hinges 210. When the loop hinges are biased as shown in FIG. 2B, the loop 206 is no longer planar with the arms 202 and/or 204 in this example and the body is at least partially twisted.

FIG. 2C illustrates that the locator 200 may be disposed on a distal end or a larger medical device. A control system 224 is provided to control operation of the locator 200. The control system 224 may include concentric tubes 220 and 222. The tube 222 may be slidably disposed inside the tube 220. The tubes 220 and 222 may be hollow. As a result, other tubes may be disposed inside one of the tubes 220 and/or 222. In addition, the tubes 220 and/or 220 may be disposed inside another tube.

In this example, the distal end of the tube 222 is connected with the distal end 218 of the locator 200. By holding the tube 220 stationary and by moving the tube 222 in a proximal direction, the distal end 218 is brought towards the proximal end 216 and the loop hinges 210 hinge from an unbiased position to a biased position. The expansion and/or contraction of the locator 200 can be performed manually, for example using a switched mechanism. The control system 224 can selectively control the distal end 218 to move the locator 200 between the unexpanded and expanded states.

Figure 3:
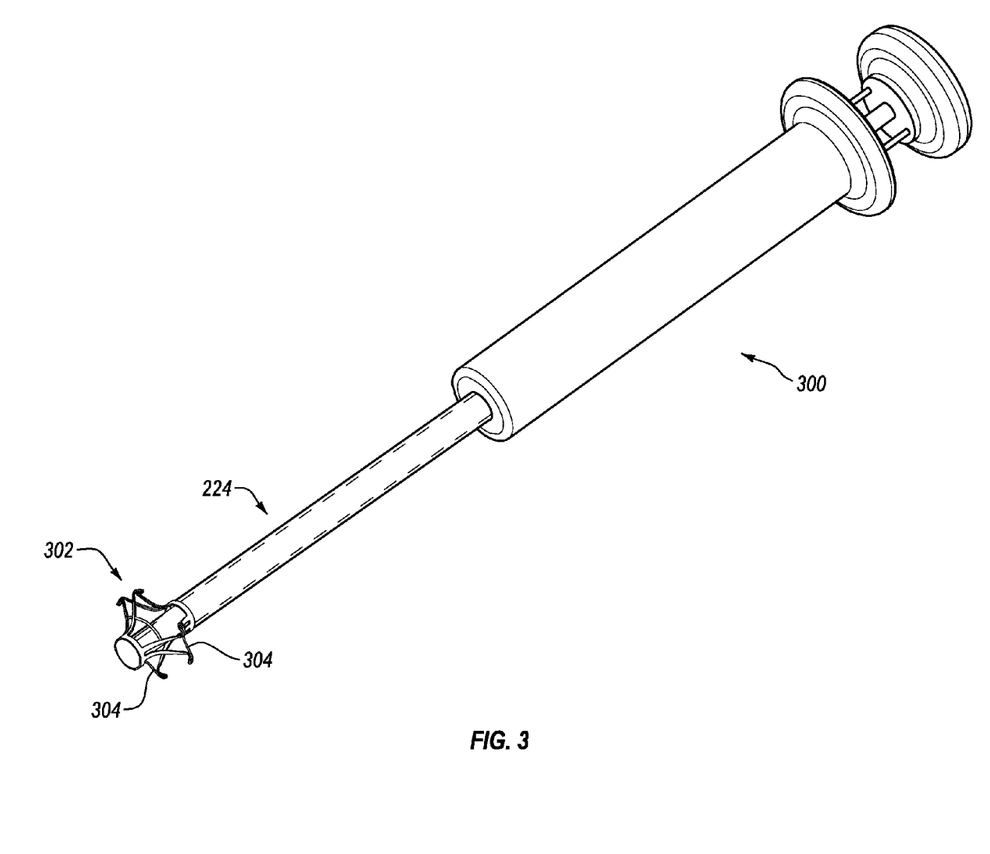
FIG. 3 illustrates a perspective view of a locator foot.

FIG. 3 illustrates a perspective view of a medical device 300 that may incorporate a device such as a loop hinge. The medical device includes a device 302 disposed on an end thereof. The medical device 302 is representative of any device that may incorporate one or more loop hinges 304. The device 302 may be a stent, a locator, a mitral clip, an embolic cage, or the like.

The foregoing examples illustrate that the loop hinge can be incorporated into larger medical devices and that the loop hinges operate by torsional movement instead of bending to accomplish a hinge between two portions of a device. The loop hinge can be oriented in any direction relative to the distal and proximal ends of the device. In one example, the loop hinge may be disposed between other components of the larger device. For example, the loop hinge can be oriented along a longitudinal axis of the larger medical device or along a different axis of the device or between other components of the device. Embodiments of the loop hinge can be integrated in any location where a hinge may be used, for example in locations that enable the device to change shape from one position to another position.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implantable prosthesis having a loop hinge comprising:
a body moveable between an unbiased position and a biased position, the body including:
a first arm having a first outer end and a first inner end;
a second arm having a second outer end and a second inner end; and
a loop connecting the first arm with the second arm,
wherein the first arm, the second arm and the loop lie in substantially the same plane in the unbiased position with the first arm and the second arm extending in opposite directions in the plane away from the loop and the loop extending in a first direction transverse to the opposite directions, and in the biased position the loop is bent at an angle out of the plane in a second direction transverse to the opposite directions,
wherein the loop is positioned at an angle relative to the first arm and the second arm, and
wherein a first torsional hinge point is formed between the first arm and a first side of the loop and a second torsional hinge point is formed between the first arm and a second side of the loop, the first torsional hinge point and the second torsional hinge point moving towards each other in a first direction as the first arm and second arm move from the unbiased position to the biased position with the loop extending in the second direction transverse to the opposite directions.

2. The implantable prosthesis of claim 1, wherein the first arm, the second arm and the loop are non-planar when in the biased position.

3. The implantable prosthesis of claim 2, wherein the body is configured to twist at the first hinge point when the first arm is rotated to the biased position and wherein the body is configured to twist at the second hinge point when the second arm is rotated.

4. The implantable prosthesis of claim 2, wherein the first hinge point is formed at a first bend in the body between the first inner end of the first arm and the first side of the loop, wherein the second hinge point is formed at a second bend in the body between second inner end of the second arm and the second side of the loop.

5. The implantable prosthesis of claim 1, wherein the first inner end of the first arm is separated from the second inner end of the second arm by a gap.

6. The implantable prosthesis of claim 5, wherein a dimension of gap changes when the loop hinge transitions from an unbiased position to a biased position.

7. The implantable prosthesis of claim 1, wherein the loop is one of circular or elliptical.

8. The implantable prosthesis of claim 1, wherein the first outer end of the first arm has a larger cross-sectional area than the first inner end of the first arm or the second outer end of the second arm has a larger cross-sectional area than the second inner end of the second arm.

9. The implantable prosthesis of claim 1, wherein the first hinge point and the second hinge point connect the loop, respectively, the first arm and the second arm such that rotation of the first arm and the second arm causes the body to twist at, respectively, the first hinge point and the second hinge point.

10. The implantable prosthesis of claim 1, wherein the body comprises a memory material.

11. An implantable prosthesis having a loop hinge comprising:
a body moveable between an unbiased position and a biased position, the body being shorter in a longitudinal direction in the biased position than in the unbiased position, the body including:
a first arm having a first outer end and a first inner end and having a first longitudinal axis;
a second arm having a second outer end and a second inner end and having a second longitudinal axis; and
a loop connecting the first arm with the second arm,
wherein the first arm and the second arm are configured to rotate relative to the loop,
wherein rotation of the first arm and the second arm twists the body to perform a hinge action that changes an orientation of the first arm relative to the second arm, and
wherein in the biased position the first arm, the second arm, and the loop are non-planar with the loop extending in a first direction transverse to the first longitudinal axis and the second longitudinal axis, a first torsional hinge point, between the first arm and the loop, and a second torsional hinge point, between the second arm, moving towards each other in a first direction as the first arm and second arm move from the unbiased position to the biased position, the loop extending in a second transverse direction that is transverse to the first direction in the biased position, a distance between peripheral edges of the loop in the first direction remaining greater than a distance between the first torsional hinge point and the second torsional hinge point in the biased position.

12. The implantable prosthesis claim 11, wherein the first arm, the second arm and the loop are arranged in a plane in an unbiased position.

13. The implantable prosthesis of claim 11, wherein the body is configured to twist at the first hinge point that joins the first arm to the loop and wherein the body is configured to twist at the second hinge point that joins the second arm to the loop.

14. The implantable prosthesis of claim 13, wherein the first hinge point is formed at a bend in the body between an inner end of the first arm and the first side of the loop.

15. The implantable prosthesis of claim 14, wherein the second hinge point is formed at a bend in the body between an inner end of the second arm and the second side of the loop.

16. The implantable prosthesis of claim 11, wherein an inner end of the first arm is separated from an inner end of the second arm by a gap.

17. The implantable prosthesis of claim 16, wherein the gap is configured to change when the loop hinge transitions from the unbiased position to the biased position.

18. The implantable prosthesis of claim 11, wherein the loop is one of circular or elliptical.

19. The implantable prosthesis of claim 11, wherein an outer end of the first arm has a larger cross-sectional area than an inner end of the first arm or an outer end of the second arm has a larger cross-sectional area than an inner end of the second arm.

20. The implantable prosthesis of claim 11, wherein the body comprises a memory material.

21. An implantable prosthesis, the device comprising:
a distal end;
a proximal end separated from the distal end; and
at least one loop hinge having a biased position and an unbiased position, the at least one loop hinge having a body comprising a first arm, a second arm, and a loop connecting the first arm with the second arm, the at least one loop hinge being disposed between the distal end and the proximal end, wherein movement of the distal end towards the proximal end twists the body into the biased position thereby hinging the at least one loop hinge such that the first arm, the second arm, and the loop are non-planar and the distal end is closer to the proximal end in the biased position, wherein, the body comprises a first torsional hinge point, between the first arm and the loop, and a second torsional hinge point, between the second arm, moving towards each other in a first movement direction as the first arm and second arm move from the unbiased position to the biased position, the loop extending in a first transverse direction transverse to directions the first arm and the second arm extend from the loop in the unbiased position and a second transverse direction transverse to the first movement direction in the biased position and forming an acute angle with the first arm and the second arm.

22. The implantable prosthesis of claim 21, wherein:
the first arm has a first outer end and a first inner end;
the second arm has a second outer end and a second inner end; and
wherein a first hinge point is formed between the loop and the first arm and wherein a second hinge point is formed between the loop and the second arm.

23. The implantable prosthesis of claim 22, wherein the first arm and the second arm are configured to rotate relative to the loop such that the body twists at the first hinge point and the second hinge point.

24. The implantable prosthesis of claim 23, wherein rotation of the first arm and the second arm twists the body to perform a hinge action that changes an orientation of the first arm relative to the second arm.

25. The implantable prosthesis of claim 24, wherein the first hinge point is formed at a bend in the body between an inner end of the first arm and the first side of the loop.

26. The implantable prosthesis of claim 22, wherein the first arm, the second arm and the loop are arranged in a plane in the unbiased position and wherein the first arm, the second arm and the loop are non-planar when in the biased position.

27. The implantable prosthesis of claim 22, wherein the at least one loop hinge comprises a first loop hinge and a second loop hinge, the first loop hinge and the second loop hinge being radially spaced apart and extending towards each other about a circumference of the device.

28. The implantable prosthesis of claim 21, wherein the device comprises a distal end of a locator device.

29. The implantable prosthesis of claim 21, wherein the device comprises a mitral clip or an embolic cage.

* * * * *